United States Patent
Bouvier et al.

(10) Patent No.: US 10,449,511 B2
(45) Date of Patent: *Oct. 22, 2019

(54) ZEOLITE ADSORBENTS WITH LOW BINDER CONTENT AND LARGE EXTERNAL SURFACE AREA, METHOD FOR PREPARATION OF SAME AND USES THEREOF

(71) Applicants: Arkema France, Colombes (FR); IFP ENERGIES NOUVELLES, Rueil-Malmaison (FR)

(72) Inventors: Ludivine Bouvier, Orthez (FR); Cecile Lutz, Gan (FR); Catherine Laroche, Vernaison (FR); Arnaud Baudot, Vernaison (FR)

(73) Assignee: Arkema France, Colombes (FR)

( * ) Notice: Subject to any disclaimer, the term of this patent is extended or adjusted under 35 U.S.C. 154(b) by 20 days.

This patent is subject to a terminal disclaimer.

(21) Appl. No.: 15/501,719

(22) PCT Filed: Aug. 4, 2015

(86) PCT No.: PCT/EP2015/067968
§ 371 (c)(1),
(2) Date: Feb. 3, 2017

(87) PCT Pub. No.: WO2016/020388
PCT Pub. Date: Feb. 11, 2016

(65) Prior Publication Data
US 2017/0239642 A1    Aug. 24, 2017

(30) Foreign Application Priority Data
Aug. 5, 2014 (FR) ..................... 14 57625

(51) Int. Cl.
| | |
|---|---|
| *B01J 20/18* | (2006.01) |
| *B01J 20/28* | (2006.01) |
| *B01J 20/04* | (2006.01) |
| *C07C 15/08* | (2006.01) |
| *B01J 20/30* | (2006.01) |
| *C07C 7/13* | (2006.01) |
| *B01D 15/18* | (2006.01) |
| *B01D 53/02* | (2006.01) |
| *B01J 20/12* | (2006.01) |

(52) U.S. Cl.
CPC ........ *B01J 20/186* (2013.01); *B01D 15/1821* (2013.01); *B01D 53/02* (2013.01); *B01J 20/04* (2013.01); *B01J 20/12* (2013.01); *B01J 20/18* (2013.01); *B01J 20/28002* (2013.01); *B01J 20/28004* (2013.01); *B01J 20/28054* (2013.01); *B01J 20/28057* (2013.01); *B01J 20/28059* (2013.01); *B01J 20/28061* (2013.01); *B01J 20/28069* (2013.01); *B01J 20/28071* (2013.01); *B01J 20/28073* (2013.01); *B01J 20/28078* (2013.01); *B01J 20/28083* (2013.01); *B01J 20/28092* (2013.01); *B01J 20/305* (2013.01); *B01J 20/3028* (2013.01); *B01J 20/3042* (2013.01); *B01J 20/3078* (2013.01); *B01J 20/3085* (2013.01); *C07C 7/13* (2013.01); *C07C 15/08* (2013.01); *B01D 2253/108* (2013.01)

(58) Field of Classification Search
CPC . B01J 20/04; B01J 20/18; B01J 20/186; B01J 20/3042; B01J 20/305; B01J 20/3078; B01J 20/28083; B01J 20/20; B01J 20/28073; B01J 20/28092; B01J 20/28002; B01J 20/28004; B01J 20/28054; B01J 20/28057; B01J 20/28059; B01J 20/28061; B01J 20/28069; B01J 20/28071; C01B 2253/108; B01D 15/1821; B01D 2253/108; C07C 7/13; C07C 15/08
USPC ... 502/60, 63, 64, 68, 69, 79, 400, 407, 411, 502/414, 415; 585/820, 824, 828; 208/310 Z
See application file for complete search history.

(56) References Cited

U.S. PATENT DOCUMENTS

| | | | |
|---|---|---|---|
| 2,985,589 A | 5/1961 | Broughton et al. | |
| 3,556,725 A | 1/1971 | Chiola et al. | |
| 3,558,730 A | 1/1971 | Neuzil | |
| 3,558,732 A | 1/1971 | Neuzil | |

(Continued)

FOREIGN PATENT DOCUMENTS

| | | |
|---|---|---|
| CN | 1267185 C | 8/2006 |
| EP | 0170299 A2 | 2/1986 |

(Continued)

OTHER PUBLICATIONS

International Search Report and Written Opinion for International Application No. PCT/EP2015/067968, dated Oct. 14, 2015, 13 Pages.

(Continued)

*Primary Examiner* — Elizabeth D Wood
(74) *Attorney, Agent, or Firm* — RatnerPrestia

(57) ABSTRACT

The present invention relates to a zeolite absorbent comprising at least one FAU zeolite with hierarchical porosity and comprising barium or barium and potassium, and the external surface area of which is greater than 20 $m^2 \cdot g^{-1}$, and the non-zeolite phase content being between 6% and 12% by weight with respect to the total weight of the absorbent. The present invention also relates to the use of such a zeolite absorbent as an adsorption agent, as well as the method for separation of para-xylene from aromatic isomer fractions with 8 carbon atoms.

20 Claims, 1 Drawing Sheet

(56) References Cited

U.S. PATENT DOCUMENTS

| | | |
|---|---|---|
| 3,626,020 A | 12/1971 | Neuzil |
| 3,663,638 A | 5/1972 | Neuzil |
| 3,878,127 A | 4/1975 | Rosback |
| 3,960,774 A | 6/1976 | Rosback |
| 4,402,832 A | 9/1983 | Gerhold |
| 4,498,991 A | 2/1985 | Oroskar |
| 5,284,992 A | 2/1994 | Hotier et al. |
| 5,629,467 A | 5/1997 | Hotier |
| 6,743,745 B2 | 6/2004 | Jaussaud et al. |
| 7,452,840 B2 | 11/2008 | Plee et al. |
| 7,785,563 B2 | 8/2010 | Ryoo et al. |
| 7,812,208 B2 | 10/2010 | Cheng et al. |
| 8,283,274 B2 | 10/2012 | Cheng et al. |
| 8,735,643 B2 | 5/2014 | Bouvier et al. |
| 2009/0326308 A1 | 12/2009 | Kulprathijanja et al. |
| 2010/0196213 A1 | 8/2010 | Lutz et al. |
| 2011/0011804 A1 | 1/2011 | Cheng et al. |
| 2011/0184165 A1 | 7/2011 | Bouvier et al. |
| 2012/0247334 A1* | 10/2012 | Hurst .................... B01D 53/02 95/147 |
| 2013/0183229 A1 | 7/2013 | Garcia-Martinez |
| 2013/0183231 A1 | 7/2013 | Senderov et al. |
| 2015/0306565 A1 | 10/2015 | Bouvier et al. |
| 2016/0207025 A1 | 7/2016 | LaRoche et al. |
| 2017/0239642 A1 | 8/2017 | Bouvier et al. |

FOREIGN PATENT DOCUMENTS

| | | |
|---|---|---|
| EP | 2592049 A2 | 5/2013 |
| FR | 2789914 A1 | 8/2000 |
| FR | 2925366 A1 | 6/2009 |
| FR | 2999098 A1 | 6/2014 |
| FR | 3010328 A1 | 3/2015 |
| FR | 3010402 A1 | 3/2015 |
| WO | 2007043731 A1 | 4/2007 |
| WO | 2008152319 A2 | 12/2008 |
| WO | 2009081023 A2 | 7/2009 |
| WO | 2013106816 A1 | 7/2013 |
| WO | 2014090771 A1 | 6/2014 |
| WO | 2015032923 A1 | 3/2015 |

OTHER PUBLICATIONS

E.P. Barrett et al., "The Determination of Pore Volume and Area Distributions in Porous Substances .I. Computations from Nitrogen Isotherms", J. Am. Chem. Soc., vol. 73, No. 1, 1951, pp. 373-380.

D. Verboekend et al., "Hierarchical Y and USY Zeolites Designed by Post-Synthetic Strategies", Adv., Funct. Mater. 22, 2012, pp. 916-928.

Choi et al., "Amphiphilic Organosilane-directed Synthesis of Crystalline Zeolite with Tunable Mesoporosity", Nature Materials, vol. 5, Sep. 2006, www.nature.com/natutematerials—pp. 718-723.

Gueudre et al., "Superior Mass Transfer Properties of Technical Zeolite Bodies with Hierarchical Porosity", Adv. Funct. Mater., 2014, 24—pp. 209-219.

Inayat et al., "Assemblies of Mesoporous FAU-Type Zeolite Nanosheets", Angewandte Chemie International Edition, 2012, 51—pp. 1962-1965.

International Search Report and Written Opinion for International Application No. PCT/FR2015/052990, dated Mar. 8, 2016—11 pages.

Non Final Office Action for U.S. Appl. No. 15/506,049, dated Nov. 2, 2018—11 pages.

Verboekend et al., "Hierarchical FAU- and LTA-Type Zeolites by Post-Synthetic Design: A New Generation of Highly Efficient Base Catalysts", Advanced Functional Materials, 2013, vol. 23, pp. 1923-1934.

Wang et al.: "Shape-controlled Synthesis of Monolithic ZSM-5 Zeolite with Hierarchical Structure and Mechanical Stability", Microporous and Mesoporous Materials, Elsevier Science Publishing, New York, US, vol. 132, No. 3, Mar. 27, 2010, pp. 428-434.

Xiao et al., "Zeolites with Hierarchically Porous Structure: Mesoporous Zeolites", Nanoscience to Catalysis, Separation, Optics, Energy, and Life Science, 1st Ed., 2012, pp. 435-455.

Verboekend et al., "Hierarchical Y and USY Zeolites Designed by Post-Synthetic Strategies", Advanced Functional Materials, 2012, vol. 22, pp. 916-928.

* cited by examiner

ZEOLITE ADSORBENTS WITH LOW BINDER CONTENT AND LARGE EXTERNAL SURFACE AREA, METHOD FOR PREPARATION OF SAME AND USES THEREOF

CROSS-REFERENCE TO RELATED APPLICATIONS

This is the national phase of International Application No. PCT/EP2015/067968, filed 4 Aug. 2015, which claims priority to French Application No. 1457625, filed 5 Aug. 2014. The disclosure of each of these applications is incorporated herein by reference in its entirety for all purposes.

FIELD OF THE INVENTION

The invention relates to zeolite adsorbents in the form of agglomerates with a low content of binder, comprising faujasite zeolite with hierarchical porosity, for their uses in applications in which material transfer is an important parameter, said adsorbents having a high outer surface area typically greater than 20 $m^2 \cdot g^{-1}$, said outer surface area being associated with a population of mesopores determined by nitrogen adsorption measurements. The term "associated" in the preceding sentence indicates that the population of mesopores contributes toward the measured outer surface area value, in addition to the outer surface area of the zeolite crystals.

The present invention also relates to a process for preparing said zeolite adsorbents, and also to the uses thereof, especially for separating gaseous or liquid mixtures of isomers, more particularly xylenes and especially for the production of very pure para-xylene from an aromatic hydrocarbon feedstock containing isomers containing 8 carbon atoms.

BACKGROUND OF THE INVENTION

The use of zeolite adsorbents comprising at least one faujasite (FAU) zeolite of type X or Y and comprising, besides sodium cations, barium, potassium or strontium ions, alone or as mixtures, for selectively adsorbing para-xylene in a mixture of aromatic hydrocarbons, is well known in the prior art.

U.S. Pat. Nos. 3,558,730, 3,558,732, 3,626,020 and 3,663,638 show that zeolite adsorbents comprising aluminosilicates based on sodium and barium (U.S. Pat. No. 3,960,774) or based on sodium, barium and potassium, are effective for separating para-xylene present in aromatic C8 fractions (fractions comprising aromatic hydrocarbons containing 8 carbon atoms).

The adsorbents described in U.S. Pat. No. 3,878,127 are used as adsorbing agents in liquid-phase processes, preferably of simulated counter-current type, similar to those described in U.S. Pat. No. 2,985,589 and which apply, inter alia, to aromatic C8 fractions.

In the patents listed above, the zeolite adsorbents are in the form of crystals in powder form or in the form of agglomerates consisting predominantly of zeolite powder and up to 20% by weight of inert binder.

The synthesis of FAU zeolites is usually performed by nucleation and crystallization of aluminosilicate gels. This synthesis leads to crystals (generally in powder form) whose use at the industrial scale is particularly difficult (substantial pressure losses during handling). Agglomerated forms of these crystals are thus preferred, in the form of grains, yarns and other agglomerates, these said forms possibly being obtained by extrusion, pelletizing, atomization and other agglomeration techniques known to those skilled in the art. These agglomerates do not have the drawbacks inherent in pulverulent materials.

Moreover, zeolite crystals are usually prepared from aqueous sodium solutions (for example aqueous sodium hydroxide solution), and, if so desired, the sodium cations may be replaced (exchanged) totally or partly with other cations, for example barium or barium and potassium. These cationic exchanges may be performed before and/or after agglomeration of the pulverulent zeolite with the agglomeration binder, according to standard techniques known to those skilled in the art.

The agglomerates, whether they are in the form of platelets, beads, extrudates or the like, generally consist of zeolite crystals, which constitute the active element (in terms of adsorption) and an agglomeration binder. This agglomeration binder is intended to ensure the cohesion of the crystals to each other in the agglomerated structure, but also should make it possible to ensure sufficient mechanical strength for said agglomerates so as to avoid, or at the very least minimize the risks of fractures, cracks or breaks that might arise during their industrial uses during which the agglomerates are subjected to numerous constraints, such as vibrations, large and/or frequent variations in pressure, movements and the like.

The preparation of these agglomerates is performed, for example, by slurrying zeolite crystals in powder form with a clay paste, in proportions from about 80% to 90% by weight of zeolite powder per 20% to 10% by weight of binder, followed by forming into beads, platelets or extrudates, and heat treatment at high temperature to bake the clay and reactivate the zeolite, the cationic exchange(s), for instance the exchange with barium and optionally with potassium, possibly taking place before and/or after agglomeration of the pulverulent zeolite with the binder.

Zeolite substances whose particle size is a few millimeters, or even of the order of a millimeter, are obtained, and which, if the choice of the agglomeration binder and the granulation are made within the rules of the art, have a satisfactory set of properties, in particular of porosity, mechanical strength and abrasion resistance. However, the adsorption properties of these agglomerates are obviously reduced when compared with the starting active powder due to the presence of agglomeration binder which is inert with respect to adsorption.

Various means have already been proposed for overcoming this drawback of the agglomeration binder being inert towards adsorption performance, among which is the transformation of all or at least part of the agglomeration binder into zeolite that is active from the point of view of adsorption. This operation is now well known to those skilled in the art, for example under the name "zeolitization". In order readily to perform this operation, zeolitizable binders are used, usually belonging to the kaolinite family, and preferably calcined beforehand at temperatures generally between 500° C. and 700° C.

Patent application FR 2 789 914 describes a process for manufacturing zeolite X agglomerates, with an Si/Al atomic ratio of between 1.15 and 1.5, exchanged with barium, and optionally with potassium, by agglomerating zeolite X crystals with a binder, a source of silica and carboxymethylcellulose, followed by zeolitizing the binder by immersing the agglomerate in an alkaline liquor. After exchange of the cations of the zeolite with barium ions (and optionally potassium ions) and activation, the agglomerates thus obtained have, from the point of view of adsorption of para-xylene contained in aromatic C8 fractions, improved properties when compared with adsorbents prepared from the same amount of zeolite X and of binder, but whose binder is not zeolitized.

U.S. Pat. No. 7,812,208 (UOP) describes a process for separating para-xylene contained in aromatic fractions, using an adsorbent of "binderless" type, i.e. without amorphous material or with an amount of less than 2% by weight of amorphous material, based on zeolite X, with a mean crystal size of less than 1.8 µm. These adsorbents are obtained after a step of zeolitization of the binder.

These adsorbents have improved transfer and adsorption properties and do not contain, or only in an amount of less than 2% by weight, and usually less than 0.5% by weight, amorphous or non-zeolitic material. On the other hand, no information is given regarding the mechanical strength of such "binderless" particles. Said document teaches that a total conversion of the binder into zeolite would make it possible to maximize the adsorption capacity. However, the mechanical properties do not always appear to be conserved or optimized in this case.

This is confirmed, for example, by patent application FR 2 999 098, which describes an agglomerated zeolite adsorbent based on zeolite X with small crystals typically less than 1.7 µm in size and which has maximum selectivity properties towards para-xylene and matter transfer properties. For this type of adsorbent, a compromise is imposed between maximum mechanical strength and optimized adsorption capacity. It also emerges in the light of the examples that even after optimum zeolitization, the smaller the size of the starting zeolite crystals (for example 0.8 µm), the weaker the mechanical strength of the agglomerated adsorbents.

The preparation processes described in the prior art involve an additional zeolitization step which, besides potentially degrading the crystallinity of small-sized crystals (<0.5 µm), entails additional costs.

Besides a high adsorption capacity and good selectivity properties towards the species to be separated from the reaction mixture, the adsorbent must have good matter transfer properties so as to ensure a sufficient number of theoretical plates for achieving efficient separation of the species in mixture, as indicated by Ruthven in the book entitled *Principles of Adsorption and Adsorption Processes*, John Wiley & Sons, (1984), pages 326 and 407. Ruthven indicates (ibid., page 243) that, in the case of an agglomerated adsorbent, the overall matter transfer depends on the addition of the intra-crystalline diffusional resistance and the diffusional resistance between the crystals.

The intra-crystalline diffusional resistance is proportional to the square of the diameters of the crystals and inversely proportional to the intracrystalline diffusivity of the molecules to be separated.

The diffusional resistance between the crystals (also known as the "micropore resistance") is itself proportional to the square of the diameters of the agglomerates, inversely proportional to the porosity contained in the macropores and mesopores (i.e. the pores whose aperture is greater than 2 nm) within the agglomerate, and inversely proportional to the diffusivity of the molecules to be separated in this porosity.

The size of the agglomerates is an important parameter during the use of the adsorbent in industrial application, since it determines the pressure loss within the industrial unit and the packing uniformity. The particle size distribution of the agglomerates should thus be narrow, and centred on number-average diameters typically between 0.40 mm and 0.65 mm so as to avoid excessive pressure losses.

The porosity contained in the macropores and mesopores may be increased by using pore-forming agents, for instance corn starch as recommended in document U.S. Pat. No. 8,283,274 for improving the matter transfer. However, this porosity does not participate in the adsorption capacity and, consequently, the improvement in the macropore matter transfer then takes place to the detriment of the volume adsorption capacity. Consequently, this approach for improving the macropore matter transfer proves to be very limited.

To estimate the improvement in the transfer kinetics, it is possible to use the plate theory described by Ruthven in *Principles of Adsorption and Adsorption Processes*, ibid., pages 248-250. This approach is based on the representation of a column by a finite number of ideally stirred hypothetical reactors (theoretical stages). The equivalent height of theoretical plates is a direct measurement of the axial dispersion and of the resistance to matter transfer of the system.

For a given zeolite structure, a given size of adsorbent and a given operating temperature, the diffusivities are fixed, and one of the means for improving the matter transfer consists in reducing the diameter of the crystals. A gain on the overall matter transfer will thus be obtained by reducing the size of the crystals.

A person skilled in the art will thus seek to minimize the diameter of the zeolite crystals in order to improve the matter transfer.

Patent CN 1267185C thus claims adsorbents containing 90% to 95% of zeolite BaX or BaKX for the separation of para-xylene, in which the zeolite X crystals are between 0.1 µm and 0.4 µm in size, in order to improve the matter transfer performance. Similarly, patent application US 2009/0 326 308 describes a process for separating xylene isomers in which the performance was improved by using adsorbents based on zeolite X crystals with a size of less than 0.5 µm.

The Applicant has nevertheless observed that the synthesis, filtration, handling and agglomeration of zeolite crystals whose size is less than 0.5 µm involve cumbersome, uneconomical processes that are thus difficult to industrialize.

Furthermore, such adsorbents comprising crystals less than 0.5 µm in size also prove to be more fragile, and it then becomes necessary to increase the content of agglomeration binder in order to reinforce the cohesion of the crystals within the adsorbent. However, increasing the content of agglomeration binder leads to densification of the adsorbents, which is the cause of an increase in the macropore diffusional resistance. Thus, despite a reduced intra-crystalline diffusional resistance due to the decrease in the size of the crystals, the increase in macropore diffusional resistance on account of the densification of the adsorbent does not allow an improvement in the overall transfer.

Moreover, increasing the binder content does not makes it possible to obtain good adsorption capacity.

The final adsorption capacity may be improved by performing, as taught in the prior art, zeolitization of the agglomeration binder of the adsorbent.

However, the beneficial effect of this binder conversion step may be greatly penalized by the degradation in crystallinity of the starting nanocrystals, this degradation being caused by the basic solutions used during this zeolitization step.

A third property of the adsorbent that is necessary for ensuring good performance of the liquid-phase separation process of simulated counter-current type is to have good mechanical strength. Specifically, under standard operating conditions of this type of process, a high mechanical stress is applied to the adsorbent in the industrial units, entailing the formation of fine particles, which induce a deterioration in the performance (see, for example, *Primary Analysis on State of Xylene Adsorption Unit*, Li et al., Jingxi Shiyou Huagong, 2004, (4), 54-55), and this being all the more the case the lower the mechanical strength of the adsorbent.

However, the prior art FR 2 999 098 shows that when small-sized crystals (for example 0.8 μm) are used, the mechanical strength also reduces, despite the zeolitization step. A person skilled in the art would thus tend to increase the size of the crystals in order to improve the mechanical strength.

In summary, for the separation of xylenes, the prior art shows that it is necessary:
1) to reduce the size of the crystals in order to improve the matter transfer,
2) and/or to increase the macroporosity by using pore-forming agents, and
3) to zeolitize the binder in order to increase the mechanical strength and maximize the adsorption capacity.

It thus appears difficult to obtain adsorbents having all the following properties combined:
the fastest possible matter transfer within the adsorbent, i.e. the smallest possible and ideally virtually zero, or even zero, resistance to matter transfer,
optimum mechanical crushing strength,
the greatest possible adsorption capacity (i.e. a content of zeolite (active crystalline phase for the purposes of adsorption) that is as large as possible).

SUMMARY OF THE INVENTION

The inventors have now discovered that the problems encountered in the prior art may be totally or at least partly solved by means of the adsorbents according to the present invention.

Figure 1:
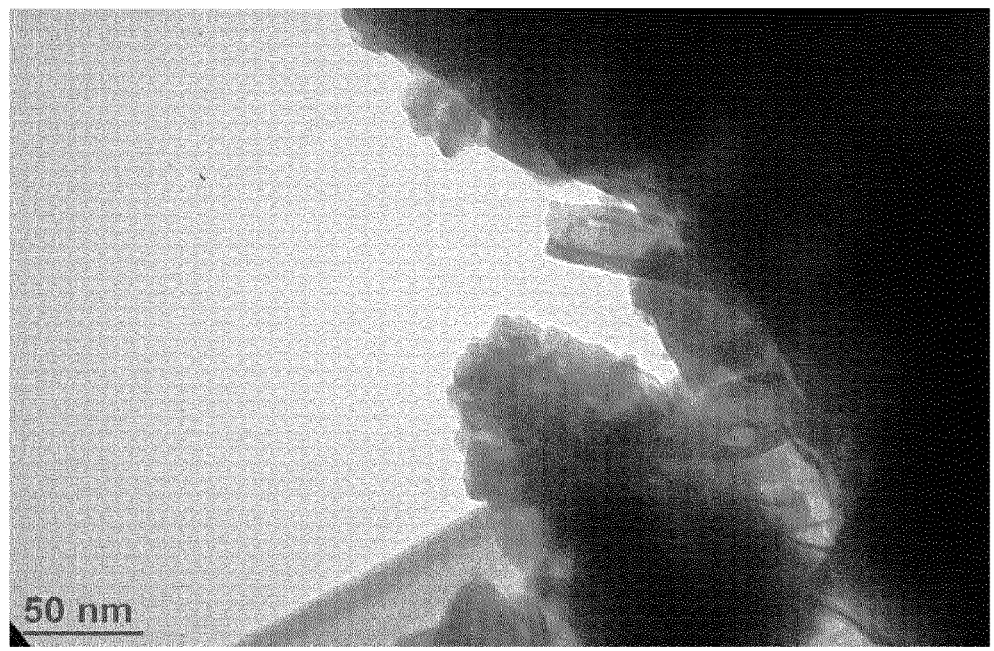
FIGS. 1 and 2 represent comparative TEM images of adsorbent materials.

In particular, one aim of the present invention consists in providing adsorbents whose matter transfer has been maximized by means of the use of zeolites:
with hierarchical porosity,
with a "conventional" crystal size, i.e. a number-average diameter of greater than or equal to 1 μm,
and whose content of binder (non-zeolitic phase) has been optimized so as to maximize the adsorption capacity while at the same time conserving mechanical properties that are compatible with their use in adsorption processes.

DETAILED DESCRIPTION OF CERTAIN EMBODIMENTS OF THE INVENTION

In the text hereinbelow, and unless otherwise indicated, the limits of a range of values are included in that range, especially in the expressions "between" and "from . . . to . . . ".

The term "zeolite with hierarchical porosity" means a zeolite containing both micropores and mesopores, in other words a zeolite that is both microporous and mesoporous. The term "mesoporous zeolite" means a zeolite whose microporous zeolite crystals have, in conjunction with the microporosity, internal cavities of nanometric size (mesoporosity), which are readily identifiable by observation using a transmission electron microscope (TEM), as described, for example, in U.S. Pat. No. 7,785,563.

The zeolite adsorbents according to the invention have a large outer surface area associated with a population of mesopores with a mean diameter of between 2 nm and 50 nm, characterized by nitrogen adsorption.

The mean diameter of the mesopores is determined via the Barrett-Joyner-Halenda method (BJH method, E. P. Barrett, L. G. Joyner, P. P. Halenda, "The Determination of Pore Volume and Area Distributions in Porous Substances. I. Computations from Nitrogen Isotherms", *J. Am. Chem. Soc.*, 73(1), (1951), 373-380), from the absorption arm of the nitrogen physisorption isotherm at 77 K.

Advantageously, the mean diameter volume distribution thus determined for the mesopores of the adsorbent according to the invention, represented graphically by dV/dDm or dV/d log Dm as a function of the mean diameter Dm, corresponds to a narrow unimodal distribution.

The term "unimodal distribution" means a distribution having only one peak. A mean diameter unimodal distribution is thus characterized by a single peak, for which the mean diameter value at the top of the peak is known as the "mode" or alternatively the "dominant value", and represents the most frequent value of the distribution. When a distribution has two peaks separated by a trough, the distribution is said to be bimodal. The invention does not relate to the case of bimodal or even multimodal distribution, i.e. distribution in which there are several zones of concentration of values separated by discontinuities. Such distributions are characteristic of the presence of several populations of pores with different mean diameters.

The term "narrow" used to characterize the mean diameter distribution of the mesopores indicates that the mid-height width of the distribution about the mode is less than 20 nm, preferably less than 15 nm, preferably between 10 nm and 0.1 nm and more preferably between 5 nm and 0.5 nm, as described later in the characterization techniques.

The use of zeolite crystals with hierarchical porosity of "conventional" size makes it possible simultaneously:
to use crystals of micrometric size (i.e. with a number-average diameter of greater than or equal to 1 μm) but with transfer properties equivalent to those obtained with very small nanometric crystals, typically with a number-average diameter strictly less than 0.5 μm, and
to conserve, for the adsorbent obtained from these zeolites with hierarchical porosity, a mechanical strength that is adapted to its use in separation processes, with a reduced content of binder(s) which makes it possible to maintain a high level in terms of adsorption capacity without necessarily having to resort to zeolitization of the binder.

As indicated previously, these zeolites with hierarchical porosity are both microporous and mesoporous, these terms having been defined earlier in the description. As indicated in U.S. Pat. No. 7,785,563, observation by transmission electron microscopy (TEM) makes it possible to check whether the zeolite crystals of the adsorbent are filled zeolite crystals (i.e. non-mesoporous) or aggregates of filled zeolite crystals or mesoporous crystals.

Another aim of the present invention consists in providing a process for preparing said adsorbents, and in particular a process for preparing said adsorbents that is more economical than the processes described in the prior art, and also the uses of said adsorbents for the separation of gaseous or liquid mixtures of isomers, more particularly xylenes and especially for the separation of very pure para-xylene from an aromatic hydrocarbon feedstock containing isomers containing 8 carbon atoms.

Yet another aim of the present invention consists in maximizing the matter transfer within the zeolite adsorbent, while at the same time maintaining an adsorption capacity that is suitable for the application, at the same time as a mechanical strength that is compatible with the application under consideration.

As yet another aim, the present invention proposes a zeolite adsorbent that is optimized for use in separation processes, combining good mechanical strength, a high adsorption capacity and maximized transport of molecules within the adsorbent and the zeolite phase (maximized matter transfer).

Thus, and according to a first aspect, the present invention relates to a zeolite adsorbent comprising at least one FAU zeolite with hierarchical porosity and comprising barium or barium and potassium, for which zeolite adsorbent:
the outer surface area, measured by nitrogen adsorption, is greater than 20 $m^2 \cdot g^{-1}$, preferably greater than 30 $m^2 \cdot g^{-1}$, and more preferably between 30 $m^2 \cdot g^{-1}$ and 200 $m^2 \cdot g^{-1}$, and more preferentially between 30 $m^2 \cdot g^{-1}$ and 150 $m^2 \cdot g^{-1}$, said outer surface area being combined with a population of mesopores with a mean diameter of between 2 nm and 50 nm, and
the content of non-zeolite phase (inert phase for the purposes of adsorption) is between 6% and 12% by weight relative to the total weight of the adsorbent, preferably between 6% and 11% by weight relative to the total weight of the adsorbent, more preferably between 6% and 10% by weight relative to the total weight of the adsorbent.

In a preferred embodiment of the invention, the FAU zeolite with hierarchical porosity of the zeolite adsorbent is a zeolite for which:
the number-average diameter of the crystals is between 1 μm and 20 μm, more preferably between 1.5 μm and 20 μm, more preferentially between 1.8 μm and 10 μm, better still between 2 μm and 10 μm and more preferably between 2 μm and 8 μm,
the outer surface area of the crystals, measured by nitrogen adsorption, is greater than 40 $m^2 \cdot g^{-1}$, preferably between 40 $m^2 \cdot g^{-1}$ and 200 $m^2 \cdot g^{-1}$ and more preferably between 40 $m^2 \cdot g^{-1}$ and 150 $m^2 \cdot g^{-1}$.

The outer surface area of the zeolite adsorbent of the invention is calculated via the t-plot method from the nitrogen adsorption isotherm at a temperature of 77 K, after degassing under vacuum ($P<6.7\times10^{-4}$ Pa), at a temperature of between 300° C. and 450° C. for a time ranging from 9 hours to 16 hours, preferably at 400° C. for 10 hours. The outer surface area of the FAU zeolite with hierarchical porosity is measured in the same manner.

According to a preferred aspect, the barium (Ba) content of the zeolite adsorbent of the invention, expressed as barium oxide (BaO), is greater than 10%, preferably greater than 15%, very preferably greater than 20%, even more preferably greater than 23%, or even greater than 33% by weight relative to the total mass of the adsorbent, and, advantageously, the barium content is between 23% and 42% and typically between 30% and 40% by weight relative to the total weight of the adsorbent.

According to another preferred aspect, the potassium (K) content of the zeolite adsorbent of the invention, expressed as potassium oxide ($K_2O$), is less than 25%, preferably between 0% and 20%, even more preferably between 0% and 15% and very preferably from 0% to 10% by weight relative to the total mass of the adsorbent.

According to yet another preferred embodiment, the total content of alkali metal or alkaline-earth metal ions, other than barium and potassium ions, expressed as the total content of alkali metal or alkaline-earth metal oxide ions other than barium oxide BaO and potassium oxide $K_2O$, is between 0 and 5% relative to the total mass of the adsorbent.

Preferably, the mesopore population of said zeolite adsorbent has mean diameters at the mode, characterized by nitrogen adsorption, of between 2 nm and 30 nm and preferably between 2 nm and 20 nm.

Advantageously, the zeolite adsorbent according to the invention has a total volume contained in the macropores and the mesopores (sum of the macropore volume and the mesopore volume), measured by mercury intrusion, of between 0.15 $cm^3 \cdot g^{-1}$ and 0.5 $cm^3 \cdot g^{-1}$, preferably between 0.20 $cm^3 \cdot g^{-1}$ and 0.40 $cm^3 \cdot g^{-1}$ and very preferably between 0.20 $cm^3 \cdot g^{-1}$ and 0.35 $cm^3 \cdot g^{-1}$.

According to a preferred embodiment of the present invention, the zeolite adsorbent simultaneously comprises macropores, mesopores and micropores. The term "macropores" means pores whose diameter is greater than 50 nm, preferably between 50 nm and 400 nm. The term "mesopores" means pores whose diameter is between 2 nm and 50 nm. The term "micropores" means pores whose diameter is less than 2 nm.

In addition, the adsorbent of the invention advantageously has a (macropore volume)/(macropore volume+mesopore volume) ratio of between 0.2 and 1 and very preferably between 0.4 and 0.8.

In the context of the present invention, a zeolite adsorbent whose micropore volume, evaluated via the t-plot method from the nitrogen ($N_2$) adsorption isotherm at a temperature of 77 K, is greater than 0.200 $cm^3 \cdot g^{-1}$, preferably between 0.205 $cm^3 \cdot g^{-1}$ and 0.270 $cm^3 \cdot g^{-1}$ and more preferably between 0.205 $cm^3 \cdot g^{-1}$ and 0.260 $cm^3 \cdot g^{-1}$ is also preferred. Said micropore volume measurement is calculated after degassing under vacuum ($P<6.7\times10^{-4}$ Pa), at a temperature of between 300° C. and 450° C. for a time ranging from 9 hours to 16 hours, preferably at 400° C. for 10 hours.

In the context of the present invention, the mechanical strength is measured by the Shell method series SMS1471-74 adapted for agglomerates less than 1.6 mm in size. This mechanical strength, measured for the zeolite adsorbent defined previously, is generally between 1.5 MPa and 4 MPa, preferably between 1.7 MPa and 4 MPa, more preferably between 1.8 MPa and 4 MPa and most preferably between 2 MPa and 4 MPa.

According to yet another preferred embodiment, the zeolite adsorbent according to the invention has an Si/Al atomic ratio of between 1.00 and 2.00, preferably between 1.00 and 1.80, more preferably between 1.15 and 1.80 and even more preferably between 1.15 and 1.60.

Among the type X FAU zeolites, it is now commonly accepted to recognize, inter alia, two subgroups known as zeolites LSX and zeolites MSX. Zeolites LSX have an Si/Al atomic ratio equal to about 1 and zeolites MSX have an Si/Al atomic ratio of between about 1.05 and about 1.15. According to a preferred embodiment, the at least one FAU zeolite is a zeolite X with an Si/Al atomic ratio of between 1.10 and 1.50. According to another preferred embodiment, the at least one zeolite X is a zeolite of LSX type with an Si/Al atomic ratio equal to about 1.

In the zeolite adsorbent of the present invention, and according to a preferred embodiment, the term "FAU zeolite with hierarchical porosity" means the X-type FAU zeolites defined above, these said zeolites having hierarchical porosity, i.e. the zeolites of X type with hierarchical porosity (or zeolites XHP), zeolites of MSX type with hierarchical porosity (or MSXHP) and zeolites of LSX type with hierarchical porosity (or LSXHP), and more particularly FAU zeolites with hierarchical porosity and an Si/Al atomic ratio of between 1.00 and 1.50, preferably between 1.05 and 1.50, more preferably between 1.05 and 1.40 and even more preferably between 1.10 and 1.40.

The invention also comprises zeolite adsorbents comprising mixtures of two or more FAU zeolites with hierarchical porosity as have just been defined.

According to another preferred embodiment, no zeolite structure other than the FAU structure, preferably no zeolite structure other than the faujasite X structure, is detected by X-ray diffraction (known to those skilled in the art under the abbreviation XRD) in the zeolite adsorbent of the present invention.

The term "no zeolite structure other than the FAU structure" means less than 2% by weight, limits inclusive, of one or more zeolite phases other than the FAU structure (mass fraction determined by XRD, technique described below).

The zeolite adsorbent according to the invention also and preferably comprises at least one non-zeolite phase (NZP) which comprises, inter alia, an agglomeration binder used in the preparation mode to ensure cohesion of the crystals, hence the term "agglomerate" or "zeolite agglomerate" occasionally used instead of the term "zeolite adsorbent" of the invention, as described previously.

In the present invention, the term "binder" means an agglomeration binder which ensures the cohesion of the zeolite crystals in the zeolite adsorbent (or agglomerated zeolite material) of the invention. This binder also differs from zeolite crystals in that it does not have a zeolite crystalline structure after calcination, which is why the binder is often termed inert, and more precisely inert with respect to adsorption and ion exchange.

According to yet another preferred embodiment, the mass fraction of FAU zeolite, FAU zeolite preferably being a type X zeolite, is greater than or equal to 88% relative to the total weight of adsorbent of the present invention, the remainder to 100% preferably consisting of non-zeolite phase (NZP).

As already indicated, the mass fraction of zeolite(s) (degree of crystallinity) of the adsorbent according to the invention may be determined by X-ray diffraction analysis, known to those skilled in the art by the abbreviation XRD.

According to a preferred embodiment, the zeolite adsorbent according to the invention has a loss on ignition, measured at 950° C. according to standard NF EN 196-2, of less than or equal to 7.7%, preferably between 0 and 7.7%, preferably between 3.0% and 7.7%, more preferably between 3.5% and 6.5% and advantageously between 4.5% and 6%.

Another subject of the invention concerns a process for preparing the zeolite adsorbent as has just been defined, said process comprising at least the steps of:

a) agglomeration of crystals of at least one FAU-type zeolite with hierarchical porosity, having an outer surface area of greater than 40 $m^2 \cdot g^{-1}$, preferably between 40 $m^2 \cdot g^{-1}$ and 200 $m^2 \cdot g^{-1}$, more preferably between 40 $m^2 \cdot g^{-1}$ and 150 $m^2 \cdot g^{-1}$, the number-average diameter of the crystals of which is between 1 µm and 20 µm, more preferably between 1.5 µm and 20 µm, more preferentially between 1.8 µm and 10 µm, better still between 2 µm and 10 µm, and more preferably between 2 µm and 8 µm, with a binder preferably comprising at least 80% of clay or of a mixture of clays and with up to 5% of additives and also with the amount of water that allows the forming of the agglomerated material, followed by drying and calcination of the agglomerates;

b) cation exchange(s) of the agglomerates from step a) by placing in contact with a solution of barium ions and/or of barium ions and potassium ions;

c) optional additional cation exchange of the agglomerates from step b) by placing in contact with a solution of potassium ions;

d) washing and drying of the agglomerates obtained in steps b) or c), at a temperature of between 50° C. and 150° C.; and e) production of the zeolite adsorbent according to the invention by activation of the agglomerates obtained in step d) under a stream of oxidizing and/or inert gas, especially with gases such as oxygen, nitrogen, air, a dry and/or decarbonated air, an oxygen-depleted air, which is optionally dry and/or decarbonated, at a temperature of between 100° C. and 400° C., preferably between 200° C. and 300° C. for a time determined as a function of the desired water content and loss on ignition, typically from 1 to 6 hours.

In a preferred embodiment of the process for preparing the zeolite adsorbent of the present invention, the drying of the agglomerates in step a) above is generally performed at a temperature of between 50° C. and 150° C., and the calcination of the dried agglomerates is generally performed under a stream of oxidizing and/or inert gas, especially with gases such as oxygen, nitrogen, air, a dry and/or decarbonated air, or an oxygen-depleted air, which is optionally dry and/or decarbonated, at a temperature above 150° C., typically between 180° C. and 800° C., preferentially between 200° C. and 650° C., for a few hours, for example from 2 hours to 6 hours.

According to a preferred embodiment, said at least one FAU zeolite is as defined and advantageously has an Si/Al atomic ratio preferably between 1.00 and 1.50, preferably between 1.05 and 1.50, more preferably between 1.05 and 1.40 and even more preferably between 1.10 and 1.40.

As indicated previously, the outer surface area of the crystals used in step a) of the process described above is calculated via the t-plot method from the nitrogen adsorption isotherm at a temperature of 77 K, after degassing under vacuum ($P<6.7\times10^{-4}$ Pa), at a temperature of between 300° C. and 450° C. for a time ranging from 9 hours to 16 hours, preferably at 400° C. for 10 hours.

The FAU zeolite crystals with hierarchical porosity with a large outer surface area may be obtained according to various methods known to those skilled in the art, for example according to the synthesis described by Inayat et al. in *Angew. Chem. Int. Ed.*, (2012), 51, 1962-1965.

It is also possible to prepare said crystals by synthesis by seeding and/or by adjusting the synthetic operating conditions such as the $SiO_2/Al_2O_3$ ratio, the sodium content and the alkalinity of the synthetic mixture or alternatively according to conventional processes for post-treatment of FAU zeolite crystals known to those skilled in the art.

The post-treatment processes generally consist in removing atoms from the already-formed zeolite network, either by one or more acid treatments which dealuminate the solid, these treatments being followed by one or more washes with sodium hydroxide (NaOH) so as to remove the aluminium-based residues formed, as described, for example, by D. Verboekend et al. (*Adv. Funct. Mater.*, 22, (2012), pp. 916-928), or alternatively by treatments which combine the action of an acid and that of a structuring agent which improve the efficacy of the acid treatment, as described, for example, in patent application WO 2013/106 816.

The processes for the direct synthesis of these zeolites (i.e. synthetic processes other than the post-treatment) generally involve one or more structuring agents or sacrificial templates.

The sacrificial templates that may be used may be of any type known to those skilled in the art and especially those described in patent application WO 2007/043 731. According to a preferred embodiment, the sacrificial template is advantageously chosen from organosilanes and more preferentially from [3-(trimethoxysilyl)propyl]octadecyldimethylammonium chloride, [3-(trimethoxy-silyl)propyl]hexadecyldimethylammonium chloride, [3-(trimethoxysilyl) propyl]dodecyl-dimethylammonium chloride, [3-(trimethoxysilyl)-propyl]octylammonium chloride, N-[3-(trimethoxysilyl)propyl]aniline, 3-[2-(2-aminoethylamino) ethylamino]propyltrimethoxy-silane, N-[3-(trimethoxysilyl) propyl]-N'-(4-vinylbenzyl)ethylenediamine, triethoxy-3-(2-imidazolin-1-yl)propylsilane, 1-[3-(trimethoxysilyl)propyl] urea, N-[3-(trimethoxy-silyl)propyl]ethylenediamine, [3-(diethylamino)propyl]trimethoxysilane, (3-glycidyloxypropyl)trimethoxysilane, 3-(trimethoxysilyl)propyl methacrylate, [2-(cyclohexenyl)ethyl]-triethoxysilane, dodecyltriethoxysilane, hexadecyltrimethoxysilane, (3-aminopropyl)trimethoxysilane, (3-mercaptopropyl) trimethoxysilane, (3-chloropropyl)trimethoxysilane, and also mixtures of two or more thereof in all proportions.

Among the sacrificial templates listed above, [3-(trimethoxysilyl)propyl]octadecyldimethylammonium chloride or TPOAC is most particularly preferred.

Use may also be made of sacrificial templates of higher molar mass, for example PPDAs (polydiallyldimethylammonium polymers), PVB (polyvinyl butyral) and other oligomeric compounds known in the field for increasing the diameter of mesopores.

According to a preferred embodiment of the process of the present invention, agglomeration of crystals of at least one FAU zeolite with hierarchical porosity, as described previously, prepared in the presence of a sacrificial template intended to be removed, is performed in step a).

This removal may be performed according to the methods known to those skilled in the art, for example by calcinations, and, in a non-limiting manner, the calcinations of zeolite crystals comprising the sacrificial template may be performed under a stream of oxidizing and/or inert gas, especially with gases such as oxygen, nitrogen, air, a dry and/or decarbonated air, or an oxygen-depleted air, which is optionally dry and/or decarbonated, at one or more temperatures above 150° C., typically between 180° C. and 800° C., preferentially between 200° C. and 650° C., for a few hours, for example between 2 and 6 hours. The nature of the gases, the temperature increase ramps and the successive temperature stages and their durations will be adapted as a function of the nature of the sacrificial template.

The additional step of removal of the optional sacrificial template may be performed at any moment during the process for preparing the zeolite adsorbent of the invention. The removal of said sacrificial template may thus advantageously be performed by calcinations of the zeolite crystals before the agglomeration step a), or alternatively concomitantly with the calcination of the adsorbent during step a).

It would not constitute a departure from the context of the invention if the agglomeration of step a) comprised the agglomeration of several FAU zeolites with hierarchical porosity obtained according to different modes.

The synthesis of FAU-type zeolite is generally performed in sodium medium (sodium hydroxide and thus $Na^+$ cation). The FAU zeolite crystals thus obtained predominantly, or even exclusively, comprise sodium cations. However, it would not constitute a departure from the context of the invention to use crystals that have undergone one or more cationic exchanges, between the system in Na form, before or after the optional removal of the sacrificial template if this step is performed before performing step a). In this case, step b) and optionally the exchange step c) consequently become unnecessary.

The size of the FAU zeolite crystals used in step a) and of the FAU zeolite crystals in the adsorbents according to the invention is measured by observation with a scanning electron microscope (SEM). As indicated previously, preferably, the mean diameter of the elements is between 1 μm and 20 μm, more preferably between 1.5 μm and 20 μm, more preferentially 1.8 μm and 10 μm, better still between 2 μm and 10 μm and more preferably between 2 μm and 8 μm. This SEM observation also makes it possible to confirm the presence of non-zeolite phase comprising, for example, agglomeration binder or any other amorphous phase in the adsorbents.

In the present document, the term "number-average diameter" or "size" is used especially for the zeolite crystals. The method for measuring these magnitudes is explained later in the description.

The agglomeration and forming (step a) may be performed according to any technique known to those skilled in the art, such as extrusion, compacting, agglomeration on a granulating plate, granulating drum, atomization and the like.

The proportions of agglomeration binder (see definition later) and of zeolite used are 8 parts to 15 parts by weight of binder per 92 parts to 85 parts by weight of zeolite. The adsorbents derived from step a), whether in the form of beads, extrudates or the like, preferably have a volume-average diameter, or their length (greatest dimension when they are not spherical), of between 0.2 mm and 2 mm, and in particular between 0.2 mm and 0.8 mm and preferably between 0.40 mm and 0.65 mm.

After step a) the finest agglomerated adsorbents may be removed by cycloning and/or screening and/or the excessively coarse agglomerates may be removed by screening or crushing, in the case of extrudates, for example.

Advantageously, the agglomeration binder is not zeolitized. The binder that may be used in the context of the present invention may thus be chosen from the conventional binders known to those skilled in the art, which may or may not be zeolitizable, and preferably chosen from clays and mixtures of clays, silicas, aluminas, colloidal silicas, alumina gels and the like, and mixtures thereof.

The clays are preferably chosen from: kaolins, kaolinites, nacrites, dickites, halloysites, attapulgites, sepiolites, montrnorillonites, bentonites, illites and metakaolins, and also mixtures of two or more thereof in all proportions.

Preference is given to fibrous clays of sepiolite or attapulgite type, the clay(s) possibly, generally, being formulated in the form of dry-ground and selected powders, or better still in the form of gel (i.e. delaminated clays) and dispersed, and optionally ground, such as the commercial clays Min-U-Gel®, Pansil®, Pangel®, Cimsil®, Attagel®, Actigel®, etc., which may or may not have undergone one or more chemical treatments. Such gels are described, for example, in EP 170 299 or U.S. Pat. No. 6,743,745.

During step a), besides the zeolite crystals, the binder may also comprise one or more additives. The additives are preferentially organic, for example lignin, starch, carboxymethylcellulose, surfactant molecules (cationic, anionic, nonionic or amphoteric), intended to facilitate the handling of the zeolite/clay paste by modification of the rheology and/or of the tack or to give the final adsorbents satisfactory properties, especially in terms of macroporosity.

Mention may be made, preferentially but not exhaustively, of methylcelluloses and derivatives thereof, lignosulfonates, polycarboxylic acids and carboxylic acid copolymers, amino derivatives thereof and salts thereof, especially alkali metal salts and ammonium salts. The additives are introduced in a proportion of from 0 to 5% and preferably from 0.1% to 2% by weight relative to the total weight of the adsorbent.

The additives may also be a source of liquid and/or solid silica, preferably representing from 1% to 5% of the total mass of said solids. The optional source of silica may be of any type known to a person skilled in the art, who is a specialist in zeolite synthesis, for example colloidal silica, diatomaceous earths, perlite, fly ash, sand, or any other form of solid silica.

For the calcination included in step a), the nature of the gases, the temperature increase ramps and the successive temperature stages, and also the respective durations thereof, will be adapted especially as a function of the nature of the sacrificial template to be removed and as a function of the nature of the binder used in the agglomeration step a).

The cation-exchange steps b) and c) described above are performed according to the conventional methods known to those skilled in the art, and usually by placing the adsorbents derived from step a) in contact with a barium and/or barium and potassium salt, such as barium chloride ($BaCl_2$) and/or potassium chloride (KCl), in aqueous solution at a temperature of between room temperature and 100° C., and preferably between 80° C. and 100° C., so as rapidly to obtain high contents of barium, i.e. contents preferably greater than 10%, preferably greater than 15%, very preferably greater than 20%, even more preferably greater than 23%, or even greater than 33%, expressed as weight of barium oxide relative to the total mass of the adsorbent.

Advantageously, the content of barium, expressed as barium oxide, is between 23% and 42% and typically between 30% and 40% by weight relative to the total weight of the adsorbent. It is preferred to work with a large excess of barium ions relative to the cations of the zeolite that it is desired to exchange, typically an excess of about 10 to 12, advantageously by performing successive exchanges.

An optional potassium exchange in step c) may be performed before and/or after the barium exchange (step b). As indicated previously, it is also possible to agglomerate in step a) FAU zeolite crystals already containing barium or potassium or barium and potassium ions (pre-exchange of the cations present in the starting FAU-type zeolite, typically sodium cations, with barium or potassium or barium and potassium ions before step a) and to dispense with (or not) steps b) and/or c).

Surprisingly, the Applicant has observed that the cation-exchange step, which may be difficult on account of the relative fragility of the structure of the zeolite crystals with hierarchical porosity, does not affect the intrinsic outer surface area and micropore volume properties (relative to the mass of the adsorbent once exchanged) of said zeolite crystals with hierarchical porosity.

After the cation-exchange step(s), washing is then performed, generally and preferably with water, followed by drying of the adsorbent thus obtained.

The activation which follows the drying is conventionally performed, according to the methods known to those skilled in the art, for example at a temperature generally of between 100° C. and 400° C., preferably between 200° C. and 300° C. for a time determined as a function of the desired water content and loss of ignition, typically from 1 to 6 hours.

The present invention also relates to the uses of the zeolite adsorbents described above as adsorption agents that can advantageously replace the adsorption agents described in the literature, based on conventional crystals of FAU-type zeolite, comprising barium or barium and potassium, or based on conventional crystals of FAU-type zeolite comprising barium or barium and potassium, and especially in the uses listed below:

separation of C8 aromatic isomer fractions and especially of xylenes,
separation of substituted toluene isomers such as nitrotoluene, diethyltoluene, toluenediamine, and the like,
separation of cresols,
separation of polyhydric alcohols, such as sugars.

The zeolite adsorbent according to the present invention especially has both a mechanical strength that is most particularly suited and an adsorption capacity that is also most particularly suited for use in processes for separating xylene isomers in the gas phase or in the liquid phase.

Thus, and according to another subject, the present invention relates to a process for separating xylene isomers in gas phase or in liquid phase using at least one zeolite adsorbent as defined previously, and preferably in which the zeolite crystals of the zeolite adsorbent are prepared by direct synthesis using one or more structural agents or sacrificial templates.

The invention especially relates to a process for separating para-xylene from aromatic isomer fractions containing 8 carbon atoms, using, as para-xylene adsorbent agent, a zeolite adsorbent as defined previously, and especially a zeolite adsorbent comprising barium and/or potassium, having a large outer surface area characterized by nitrogen adsorption, typically greater than 20 $m^2 \cdot g^{-1}$, preferably greater than 30 $m^2 \cdot g^{-1}$ and more preferably between 30 $m^2 \cdot g^{-1}$ and 200 $m^2 \cdot g^{-1}$, and more preferentially between 30 $m^2 \cdot g^{-1}$ and 150 $m^2 \cdot g^{-1}$, used in liquid-phase processes, but also in gas-phase processes.

The desired product (para-xylene) may thus be separated out by preparative adsorption liquid chromatography (in batch form), and advantageously continuously on a simulated moving bed, i.e. in simulated counter-current or in simulated co-current, and more particularly in simulated counter-current.

The operating conditions of an industrial adsorption unit of simulated counter-current type are generally the following:

number of beds: 6 to 30,
number of zones: at least 4 operating zones, each being located between a feed point and a withdrawal point,
temperature between 100° C. and 250° C., preferably between 150° C. and 190° C.,
pressure of the industrial unit between the bubble pressure of xylenes at the process temperature and 3 MPa,
ratio of the desorbent/feedstock flow rates of between 0.7 and 2.5, for example between 0.9 and 1.8 for a single (stand-alone) adsorption unit and between 0.7 and 1.4 for an adsorption unit combined with a crystallization unit,
recycle ratio of between 2 and 12, preferably between 2.5 and 6.0.

Reference may also be made to the teaching of patents U.S. Pat. Nos. 2,985,589, 5,284,992 and 5,629,467.

The operating conditions of an industrial simulated co-current adsorption unit are generally the same as those functioning with simulated counter-current except for the degree of recycling, which is generally between 0.8 and 7. Reference may be made to patents U.S. Pat. Nos. 4,402,832 and 4,498,991.

The desorption solvent may be a desorbent known to those skilled in the art and whose boiling point is less than that of the feedstock, such as toluene, but also a desorbent whose boiling point is greater than that of the feedstock, such as para-diethylbenzene (PDEB). The selectivity of the adsorbents according to the invention for the adsorption of the para-xylene contained in $C_8$ aromatic fractions is optimal when their loss on ignition measured at 950° C. is preferably less than or equal to 7.7%, preferably between 0 and 7.7%, very preferably between 3.0% and 7.7%, more preferably between 3.5% and 6.5% and even more preferably between 4.5% and 6%.

The para-xylene separation process according to the present invention has essential advantages over those known in the prior art, and among which is especially that of affording a most particularly advantageous compromise between satisfactory adsorption capacity by virtue in particular of a reduced content of non-zeolite phase typically of 6% to 12% by weight of binder, relative to the total weight of the adsorbent, and good mechanical strength, measured by the Shell method series SMS1471-74 adapted for agglomerates smaller than 1.6 mm in size, typically between 1.5 MPa and 4 MPa, preferably between 1.7 MPa and 4 MPa, more preferably between 1.8 MPa and 4 MPa and entirely preferably between 2 MPa and 4 MPa.

In addition, it has been noted that the outer surface area (typically greater than 20 $m^2 \cdot g^{-1}$ as indicated previously) makes it possible to reduce the time of transport to the micropores, leading to a significantly improved matter transfer relative to the prior art.

Moreover, since a zeolitization step, which is often recommended in the prior art to maximize the zeolite content of zeolite adsorbents, is not necessary with the zeolite adsorbents of the present invention, the process for preparing said zeolite adsorbents has many particularly sought advantages, among which mention may be made of the gains in costs, the gains in process times, a significant reduction in the degradation of the crystals by basic solutions, as is often the case during zeolitization operations especially during the use of nanometric-sized crystals.

Another advantage is that of having available micrometric-sized crystals (typically between 1 μm and 20 μm, more preferably between 1.5 μm and 20 μm, more preferentially between 1.8 μm and 10 μm, better still between 2 μm and 10 μm and more preferably between 2 μm and 8 μm) which are readily manipulable, thus making the manufacture of adsorbents easier.

Thus, the zeolite adsorbents of the invention especially have improved matter transfer properties while at the same time maintaining optimum properties of selectivity towards para-xylene and maximum adsorption capacity, and conserving a high mechanical strength for use in a solid-phase para-xylene separation process, preferably of simulated counter-current type.

Characterization Techniques
Particle Size of the Zeolite Crystals—Detection of the Mesopores:

The estimation of the number-average diameter of the zeolite FAU crystals contained in the zeolite adsorbents according to the invention is performed by observation with a scanning electron microscope (SEM).

In order to estimate the size of the zeolite crystals in the adsorbents, a set of images is taken at a magnification of at least 5000. The diameter of at least 200 crystals is then measured using dedicated software. The accuracy is of the order of 3%.

Figure 2:
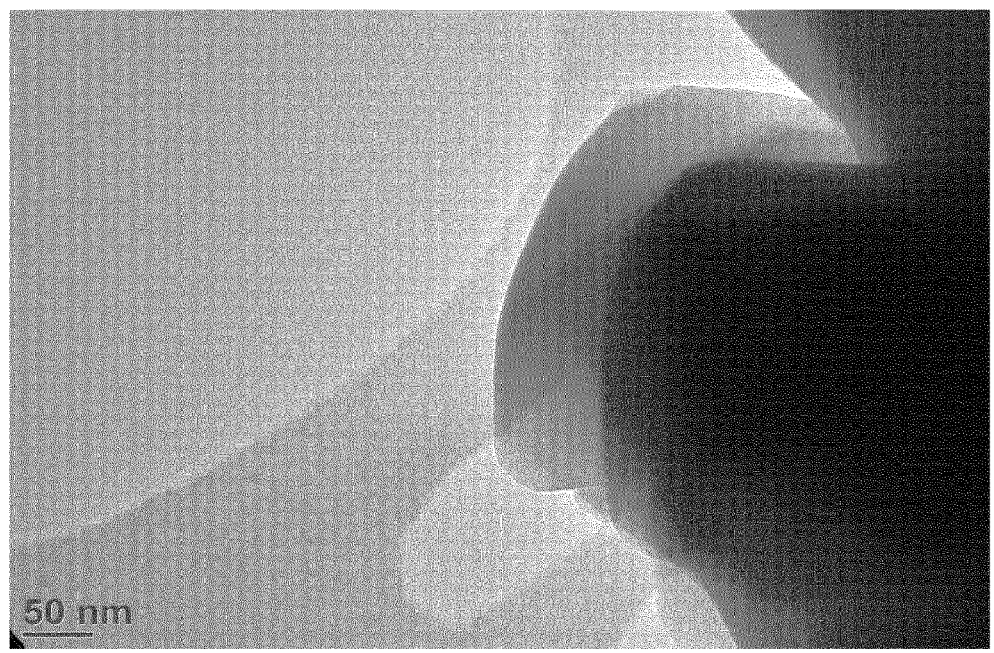

As indicated in U.S. Pat. No. 7,785,563, TEM also makes it possible to check whether the zeolite crystals contained in the adsorbent are filled zeolite crystals (i.e. non-mesoporous) or aggregates of filled zeolite crystals or mesoporous crystals (cf. the comparison of the TEM images in FIG. 1, in which the mesoporosity is clearly visible, and FIG. 2 which show filled crystals). TEM observation thus makes it possible to visualize the presence or absence of the mesopores. Preferably, the adsorbents of the process according to the invention very predominantly contain, i.e. typically more than 80% and preferably more than 90% by number, mesoporous zeolite crystals rather than filled crystals. This statistical analysis is advantageously performed by analysing at least 50 TEM or SEM images (SEM on sections of samples obtained by ionic polishing).

Chemical Analysis of the Zeolite Adsorbent—Si/Al Ratio and Degree of Exchange:

An elemental chemical analysis of the zeolite adsorbent may be performed according to various analytical techniques known to those skilled in the art. Among these techniques, mention may be made of the technique of X-ray fluorescence chemical analysis as described in standard NF EN ISO 12677: 2011 on a wavelength dispersive spectrometer (WDXRF), for example the Tiger S8 machine from the company Bruker.

X-ray fluorescence is a non-destructive spectral technique exploiting the photoluminescence of atoms in the X-ray range, to establish the elemental composition of a sample. Excitation of the atoms, generally with a beam of X-rays or by bombardment with electrons, generates specific radiations after returning to the ground state of the atom. The X-ray fluorescence spectrum has the advantage of depending very little on the chemical combination of the element, which offers a precise determination, both quantitatively and qualitatively. A measuring uncertainty of less than 0.4% by weight is conventionally obtained after calibration for each oxide.

These elemental chemical analyses make it possible both to check the Si/Al atomic ratio of the zeolite used during the preparation of the adsorbent, and also the Si/Al atomic ratio of the adsorbent and to check the quality of the ion exchange described in step b) and the optional step c). In the description of the present invention, the measuring uncertainty of the Si/Al atomic ratio is ±5%.

The quality of the ion exchange is linked to the number of moles of sodium oxide, $Na_2O$, remaining in the zeolite agglomerate after exchange. More specifically, the degree of exchange with barium ions is estimated by evaluating the ratio between the number of moles of barium oxide, BaO, and the number of moles of the combination ($BaO+Na_2O$). Similarly, the degree of exchange with barium and/or potassium ions is estimated by evaluating the ratio between the number of moles of the combination barium oxide+potassium oxide ($BaO+K_2O$) and the number of moles of the combination ($BaO+K_2O+Na_2O$). It should be noted that the contents of various oxides are given as weight percentages relative to the total weight of the anhydrous zeolite adsorbent.

Particle Size of the Zeolite Adsorbents:

The determination of the volume-average diameter of the zeolite adsorbents obtained after the agglomeration and forming step a) is performed by analysis of the particle size distribution of a sample of adsorbent by imaging according to standard ISO 13322-2:2006, using a conveyor belt which allows the sample to pass before the objective lens of the camera.

The volume-average diameter is then calculated from the particle size distribution by applying standard ISO 9276-2:2001. In the present document, the name "volume-average diameter" or "size" is used for the zeolite adsorbents. The precision is of the order of 0.01 mm for the range of sizes of the adsorbents that are useful in the context of the present invention.

Mechanical Strength of the Zeolite Adsorbents:

The crush strength of a bed of zeolite adsorbents as described in the present invention is characterized according to the Shell method series SMS1471-74 (Shell Method Series SMS1471-74 *Determination of Bulk Crushing Strength of Catalysts. Compression-Sieve Method*), associated with the BCS Tester machine sold by the company Vinci Technologies. This method, initially intended for the characterization of catalysts from 3 mm to 6 mm, is based on the use of a 425 μm screen, which makes it possible especially to separate the fines created during the crushing. The use of a 425 μm screen remains suited to zeolite adsorbents with a diameter of greater than 1.6 mm, but should be adapted according to the particle size of the adsorbents that it is desired to characterize.

The adsorbents of the present invention, generally in the form of beads or extrudates, generally have a volume-average diameter or a length, i.e. longest dimension in the case of non-spherical adsorbents, of between 0.2 mm and 2 mm, in particular between 0.2 mm and 0.8 mm and preferably between 0.40 mm and 0.65 mm. Consequently, a 100 μm screen is used instead of the 425 μm screen mentioned in the Shell method standard SMS1471-74.

The measuring protocol is as follows: a sample of 20 cm³ of agglomerated adsorbents, screened beforehand with the appropriate screen (100 μm) and dried beforehand in an oven for at least 2 hours at 250° C. (instead of 300° C. mentioned in Shell method standard SMS1471-74), is placed in a metal cylinder of known internal cross section. An increasing force is imposed in stages on this sample by means of a piston, through a bed of 5 cm³ of steel balls so as better to distribute the force exerted by the piston on the agglomerated absorbents (use of balls 2 mm in diameter for particles of spherical shape with a diameter strictly less than 1.6 mm). The fines obtained at the various pressure stages are separated out by screening (appropriate 100 μm screen) and weighed.

The bulk crushing strength is determined by the pressure in megapascals (MPa) for which the cumulative amount of fines passing through the screen is 0.5% by weight of the sample. This value is obtained by plotting on a graph the mass of fines obtained as a function of the force applied to the adsorbent bed and by interpolating to 0.5% by mass of cumulative fines. The mechanical bulk crushing strength is typically between a few hundred kPa and a few tens of MPa and generally between 0.3 MPa and 3.2 MPa. The precision is conventionally less than 0.1 MPa.

Non-Zeolite Phase of the Zeolite Adsorbents:

The content of non-zeolite phase NZP, for example the content of agglomeration binder and of any other amorphous phase, is calculated according to the following equation:

$$NZP = 100 - \Sigma(ZP),$$

in which ZP represents the sum of the amounts of zeolite X fractions within the meaning of the invention.

Mass Amount of the Zeolite Fractions of the Zeolite Adsorbents:

The mass amount of the zeolite fractions is measured by X-ray diffraction analysis, known to those skilled in the art by the abbreviation XRD. This analysis is performed on a Brüker brand machine, and the amount of zeolite fractions is then evaluated from the peak intensities of the diffractograms by taking as reference the peak intensities of a suitable reference (zeolite of the same chemical nature assumed to be 100% crystalline under cationic treatment conditions identical to those of the adsorbent under consideration). The peaks for tracing back to the crystallinity are the most intense peaks of the angular 2θ zone between 9° and 37°, namely peaks observed in the angular 2θ ranges between, respectively, 11° and 13°, between 22° and 26° and between 31° and 33°.

Micropore Volume, Outer Surface Area and Diameter of the Mesopores:

The crystallinity of the zeolite adsorbents of the invention is also evaluated by measuring their micropore volume and comparing it with that of a suitable reference (100% crystalline zeolite under identical cationic treatment conditions or theoretical zeolite). This micropore volume is determined form the measurement of the adsorption isotherm of the gas, such as nitrogen, at its liquefaction temperature.

Prior to the adsorption, the zeolite adsorbent is degassed at between 300° C. and 450° C. for a time of between 9 hours and 16 hours under vacuum ($P < 6.7 \times 10^{-4}$ Pa). Measurement of the nitrogen adsorption isotherm at 77 K is then performed on an ASAP 2020 M machine from Micromeritics, taking at least 35 measurement points at relative pressures with a ratio $P/P_0$ of between 0.002 and 1.

The micropore volume and the outer surface area are determined from the isotherm obtained, via the t-plot method by applying standard ISO 15901-3:2007 and calculating the statistical thickness t via the Harkins-Jura equation. The micropore volume and the outer surface area are obtained by linear regression on the points of the t-plot between 0.45 nm and 0.57 nm, respectively from the y-axis to the origin and from the slope of the linear progression. The evaluated micropore value is expressed in cm³ of liquid adsorbate per gram of anhydrous adsorbent. The outer surface area is expressed in m² per gram of anhydrous adsorbent.

Interpretation of the nitrogen adsorption isotherm at 77 K via the Barrett-Joyner-Halenda method (BJH method, proposed in 1951) also makes it possible to obtain the pore size distribution, and especially the mesopore distribution. The mesopore size distribution by volume is represented by the curve dV/dDm as a function of the mean pore diameter Dm.

The full width at half maximum of the volume distribution dV/dDm is given by the difference between the two mean diameters for which the value dV/dDm would be equal to half of its maximum value $f_{max}$, at the top of the peak. These two mean diameters are obtained by interpolation between the desired points on either side of the mode, for which dV/dDm surrounds the value $f_{max}/2$. This is the full width at half maximum or FWHM of a distribution f(x) whose maximum value is $f_{max}$.

Macropore and Mesopore Volume and Grain Density:

The macropore and mesopore volumes and the grain density are measured by mercury intrusion porosimetry. An Autopore® 9500 mercury porosimeter from Micromeritics is used to analyse the distribution of the pore volume contained in the macropores and in the mesopores.

The experimental method, described in the operating manual for the machine which refers to standard ASTM D4284-83, consists in placing a sample of adsorbent (zeolitic granular material to be measured) (known loss on ignition) weighed beforehand, in a porosimeter cell, and then, after first degassing (vacuum pressure of 30 µmHg for at least 10 minutes), in filling the cell with mercury at a given pressure (0.0036 MPa) and then in applying a pressure increasing in stages up to 400 MPa so as to make the mercury gradually penetrate into the pore network of the sample.

The relationship between the applied pressure and the apparent pore diameter is established by assuming cylindrical pores, a contact angle between the mercury and the pore wall of 140° and a mercury surface tension of 485 dynes/cm. The cumulative amount of mercury introduced as a function of the applied pressure is recorded. The value at and above which the mercury fills all the inter-granular voids is set at 0.2 MPa, and it is considered that beyond this value, the mercury penetrates into the pores of the granular material. The grain volume (Vg) is then calculated by subtracting the cumulative volume of mercury at this pressure (0.2 MPa) from the volume of the porosimeter cell, and by dividing this difference by the mass of the anhydrous equivalent granular material, i.e. the mass of said material corrected for the loss on ignition.

The grain density is the inverse of the grain volume (Vg), and is expressed in grams of anhydrous adsorbent per cm$^3$.

The macropore volume of the granular material is defined as being the cumulative volume of mercury introduced at a pressure of between 0.2 MPa and 30 MPa, corresponding to the volume contained in the pores with an apparent diameter of greater than 50 nm. The mesopore volume of the granular material is defined as being the cumulative volume of mercury introduced at a pressure of between 30 MPa and 400 MPa.

In the present document, the macropore and mesopore volumes of the zeolite adsorbents, expressed in cm$^3 \cdot$g$^{-1}$, are thus measured by mercury intrusion and related to the mass of the sample as anhydrous equivalent, i.e. the mass of said material corrected for the loss on ignition.

Loss on Ignition of the Zeolite Adsorbents:

The loss on ignition is determined under an oxidizing atmosphere, by calcination of the sample in air at a temperature of 950° C.±25° C., as described in standard NF EN 196-2 (April 2006). The measurement standard deviation is less than 0.1%.

Example A: Synthesis of FAU Zeolite with Hierarchical Porosity

The FAU zeolite with a high outer surface area is synthesized directly according to the article by Inayat et al. (*Angew. Chem. Int. Ed.*, (2012), 51, 1962-1965).

Step 1): Preparation of the Growth Gel in a Reactor Stirred with an Archimedean Screw at 300 rpm.

A growth gel is prepared in a stainless-steel reactor equipped with a heating jacket, a temperature probe and a stirrer, by mixing a solution of aluminate containing 119 g of sodium hydroxide (NaOH) with 128 g of alumina trihydrate ($Al_2O_3$, $3H_2O$, containing 65.2% by weight of $Al_2O_3$) and 195.5 g of water at 25° C. over 25 minutes with a stirring speed of 300 rpm in a silicate solution containing 565.3 g of sodium silicate, 55.3 g of NaOH and 1997.5 g of water at 25° C.

The stoichiometry of the growth gel is as follows: 3.48 $Na_2O/Al_2O_3/3.07$ $SiO_2/180$ $H_2O$. Homogenization of the growth gel is performed with stirring at 300 rpm for 25 minutes at 25° C.

Step 2): Introduction into the Reaction Medium of the Structuring Agent 27.3 g of TPOAC at 60% in MeOH are introduced into the reaction medium with a stirring speed of 300 rpm (TPOAC/$Al_2O_3$ mole ratio=0.04). After homogenization for 5 minutes, the stirring speed is lowered to 50 rpm.

Step 3): Maturation Phase

The reaction medium is stirred at 50 rpm at 25° C. for 22 hours, and crystallization is then started.

Step 4): Crystallization

The stirring speed is maintained at 50 rpm, and the nominal temperature of the reactor jacket is set at 80° C. so that the temperature of the reaction medium rises to 75° C. over 80 minutes. After 72 hours at a stage of 75° C., the reaction medium is cooled by circulating cold water in the jacket to stop the crystallization.

Step 5): Filtration/Washing

The solids are recovered on a sinter and then washed with deionized water to neutral pH.

Step 6): Drying/Calcination

In order to characterize the products, drying is performed in an oven at 90° C. for 8 hours; the loss on ignition of the dried product is 22% by weight.

Calcination of the dried product, which is necessary to release both the microporosity (water) and the mesoporosity by removing the structuring agent, is performed with the following temperature profile: 30 minutes of increase to 200° C., followed by 1 hour at a stage of 200° C., then 3 hours of increase to 550° C., and finally 1.5 hours at a stage of 550° C.

The micropore volume and the outer surface area measured according to the t-plot method from the nitrogen adsorption isotherm at 77 K after degassing under vacuum at 400° C. for 10 hours are, respectively, 0.260 cm$^3 \cdot$g$^{-1}$ and 90 m$^2 \cdot$g$^{-1}$. The number-average diameter of the crystals of the mesoporous zeolite (or zeolite with hierarchical porosity) thus obtained is 4.5 µm and the Si/Al ratio is equal to 1.24.

In the text hereinbelow, a mass expressed as anhydrous equivalent means a mass of product minus its loss on ignition.

Example 1: (Comparative)

Preparation of a Zeolite Adsorbent in the Form of Beads with a Zeolite of XHP Type, Zeolite Crystals 4.5 µm in Size and a Binder of Kaolin Type Such that the Content of Non-Zeolite Phase (NZP) of the Final Adsorbent is Equal to 16% by Weight Relative to the Total Weight of the Adsorbent.

A homogenous mixture is prepared consisting of 1600 g anhydrous equivalent of zeolite X crystals synthesized according to the procedure of Example A (crystal size 4.5 µm), 350 g anhydrous equivalent of kaolin, 130 g of colloidal silica sold under the trade name Klebosol® 30 (containing 30% by weight of $SiO_2$ and 0.5% of $Na_2O$) and also the amount of water that allows agglomeration of the mixture according to bead formation techniques, for instance granulating plate.

Distribution beads between 0.3 mm and 0.8 mm and with a volume-average diameter of 0.55 mm are formed. The beads are dried overnight in a ventilated oven at 80° C. They are then calcined for 2 hours at 550° C. under a stream of nitrogen, and then for 2 hours at 550° C. under a stream of decarbonated dry air.

Barium exchange is then performed with a 0.7M concentration of barium chloride solution, $BaCl_2$, at 95° C. in 4 steps. At each step, the volume ratio of solution to mass of solid is 20 ml/g and the exchange is continued for 4 hours each time. Between each exchange, the solid is washed several times so as to free it of the excess salt. It is then dried at 80° C. for 2 hours and then activated at 250° C. for 2 hours under a stream of nitrogen.

The degree of barium exchange measured by WDXRF, as described above in the analytical techniques, is 97% and the loss on ignition (measured at 900° C.) is 5.5%. The micropore volume and the outer surface area measured according to the t-plot method from the nitrogen adsorption isotherm at 77 K after degassing under vacuum at 400° C. for 10 hours are, respectively, 0.192 $cm^3 \cdot g^{-1}$ and 70 $m^2 \cdot g^{-1}$.

The total volume contained in the macropores and the mesopores (sum of the macropore volume and of the mesopore volume) measured by mercury intrusion is 0.31 $cm^3 \cdot g^{-1}$. The (macropore volume)/(macropore volume+mesopore volume) ratio is equal to 0.65.

The content of non-zeolite phase of the 97% barium-exchanged adsorbent is 16% by weight relative to the total weight of the adsorbent.

Example 2

Adsorbent with XHP Crystals 4.5 μm in Size and an Agglomeration Binder of Kaolin Type Such that the Content of Non-Zeolite Phase of the Final Adsorbent is Between 4% and 20% by Weight Relative to the Total Weight of the Adsorbent.

Example 1 is reproduced, varying the content of agglomeration binder so as to obtain adsorbents whose content of non-zeolite phase after exchange ranges between 4% and 20%. The adsorbents are subjected to the same treatments as in Example 1. The results are collated in Table 1 below:

TABLE 1

| Ex. | NZP content (%) | REL (Mpa) | $V_{micro}$ by t-plot ($cm^3 \cdot g^{-1}$) |
|---|---|---|---|
| comparative | 4 | 0.5 | 0.220 |
| comparative | 5 | 1.0 | 0.211 |
| according to the invention | 6 | 1.6 | 0.215 |
| according to the invention | 8 | 1.8 | 0.211 |
| according to the invention | 10 | 2.0 | 0.206 |
| according to the invention | 12 | 2.2 | 0.202 |
| comparative | 16 | 2.4 | 0.192 |
| comparative | 20 | 3.0 | 0.183 |

A piercing test (frontal chromatography) is then performed on a selection of 6 adsorbents to evaluate their efficacy. The adsorbents containing 4% and 5% NZP are not tested, since such adsorbents could not be used in the para-xylene separation application on account of their low mechanical strength. The amount of adsorbent used for this test is about 34 g. The loss on ignition (LOI) is set at between 5.4% and 5.6%.

The procedure for obtaining the piercing curves is as follows:

packing of the column with the sieves and installation in the test bed;
packing with the solvent at room temperature;
gradual rise to 175° C. under a stream of solvent (5 $cm^3 \cdot min^{-1}$);
injection of solvent at 30 $cm^3 \cdot min^{-1}$ when the adsorption temperature (175° C.) is reached;
solvent/feedstock exchange to inject the feedstock (30 $cm^3 \cdot min^{-1}$);
collection and analysis of the piercing effluent; the injection of the feedstock will be maintained until the concentration of solvent in the effluent is zero.

The solvent used is para-diethylbenzene. The composition of the feedstock is as follows:
para-xylene: 45% by weight,
meta-xylene: 45% by weight,
isooctane: 10% by weight (this is used as tracer for estimating the non-selective volumes and does not participate in the separation).

The pressure is sufficient for the feedstock to remain in liquid phase at the adsorption temperature, i.e. 1 MPa. The surface speed is 1.3 cm/s.

The selectivity of para-xylene relative to meta-xylene is calculated from the adsorbed amounts of each compound, the latter being determined by material balance from the first moments of the piercing curves for all of the constituents present in the effluent. The evaluation of the quality of the matter transfer is performed by estimating the EHTPs from the para-xylene piercing curves. The results are given in Table 2 below:

TABLE 2

| Example | NZP content (%) | Xylene adsorption capacity ($cm^3 \cdot g^{-1}$) | PX transfer (=EHTP) |
|---|---|---|---|
| according to the invention | 6 | 0.205 | 4.4 |
| according to the invention | 8 | 0.200 | 4.6 |
| according to the invention | 10 | 0.194 | 4.7 |
| according to the invention | 12 | 0.189 | 5.1 |
| comparative | 16 | 0.181 | 5.4 |
| comparative | 20 | 0.172 | 6.8 |

In the above table:
the xylene adsorption capacity is expressed in $cm^3$ of aromatic C8 adsorbed per gram of adsorbent;
"PX" means para-xylene; and finally
"EHTP" represents the equivalent height of theoretical plates and is expressed in cm.

The adsorbents comprising 16% and 20% by weight of NZP have a loss of adsorption capacity of greater than 10% relative to the adsorbent with the highest xylene adsorption capacity (0.205 $cm^3 \cdot g^{-1}$). Moreover, the increase in the diffusional resistance to PX transfer (EHTP) is increasingly pronounced beyond 12% NZP.

The invention claimed is:

1. A zeolite adsorbent comprising at least one FAU zeolite with hierarchical porosity and comprising barium, wherein the zeolite adsorbent has:
micropores,
mesopores with a mean diameter of between 2 nm and 50 nm,
an outer surface area, measured by nitrogen adsorption, of greater than 20 $m^2 \cdot g^{-1}$, and a content of non-zeolite phase of between 6% and 12% by weight relative to the total weight of the adsorbent.

2. The zeolite adsorbent according to claim 1, wherein the FAU zeolite with hierarchical porosity of the zeolite adsorbent is a zeolite in the form of crystals having:
a number-average diameter of between 1 μm and 20 μm, an outer surface area, measured by nitrogen adsorption, greater than 40 $m^2 \cdot g^{-1}$.

3. The zeolite adsorbent according to claim 1, having a total volume contained in the macropores and the mesopores (sum of the macropore volume and of the mesopore volume) measured by mercury intrusion of between 0.15 $cm^3 \cdot g^{-1}$ and 0.5 $cm^3 \cdot g^{-1}$.

4. The zeolite adsorbent according to claim 1, having a (macropore volume)/(macropore volume+mesopore volume) ratio of between 0.2 and 1.

5. The zeolite adsorbent according to claim 1, having a mass fraction of FAU zeolite greater than or equal to 88% relative to the total weight of adsorbent of the present invention, the remainder to 100% consisting of non-zeolite phase.

6. A process for preparing a zeolite adsorbent according to claim 1, said process comprising at least the steps of:
a) agglomeration of agglomerating crystals of at least one FAU-type zeolite with hierarchical porosity, having an outer surface area of greater than 40 $m^2 \cdot g^{-1}$, the number-average diameter of the crystals being between 1 μm and 20 μm, with a binder and also with the amount of water that allows the forming of an agglomerated material, followed by drying and calcination of the agglomerated material to obtain agglomerates;
b) cation exchanging of the agglomerates from step a) by placing in contact with a solution comprising barium ions;
c) optional additional cation exchanging of the agglomerates from step b) by placing in contact with a solution comprising potassium ions;
d) washing and drying of the agglomerates obtained in steps b) or c), at a temperature of between 50° C. and 150° C.; and
e) producing the zeolite adsorbent according to claim 1 by activating the agglomerates obtained in step d) under a stream of oxidizing and/or inert gas, at a temperature of between 100° C. and 400° C.

7. The process according to claim 6, wherein, prior to step a), the at least one FAU zeolite with hierarchical porosity is prepared in the presence of a sacrificial template that is intended to be removed.

8. The process according to claim 6, wherein the agglomeration and the forming (step a) are performed according to one or more of the techniques selected from the group consisting of extrusion, compacting, agglomeration on a granulating plate, granulating drum, and atomization.

9. The process according to claim 6, wherein agglomeration binder and zeolite are used in a proportion of from 8 parts to 15 parts by weight of binder per 92 parts to 85 parts by weight of zeolite.

10. The process according to claim 6, wherein the binder is selected from the group consisting of clays and mixtures of clays, silicas, aluminas, colloidal silicas and alumina gels, and mixtures thereof.

11. The process according to claim 10, wherein the binder is a clay selected from the group consisting of kaolins, kaolinites, nacrites, dickites, halloysites, attapulgites, sepiolites, montmorillonites, bentonites, illites and metakaolins, and also mixtures of two or more, in all proportions.

12. The process according to claim 11, wherein the clay(s) are formulated in the form of dry-ground and selected powders, or in the form of gel, and dispersed, and optionally ground.

13. A process for separating xylene isomers in gas phase or in liquid phase comprising contacting xylene isomers in gas phase or liquid phase with at least one zeolite adsorbent according to claim 1.

14. The process according to claim 13, wherein the process is a process for separating para-xylene from aromatic isomer fractions containing 8 carbon atoms.

15. The zeolite adsorbent according to claim 1, wherein the outer surface of the zeolite adsorbent, measured by nitrogen adsorption, is between 30 $m^2 \cdot g^{-1}$ and 200 $m^2 \cdot g^{-1}$.

16. The zeolite adsorbent according to claim 1, wherein the outer surface of the zeolite adsorbent, measured by nitrogen adsorption, is between 30 $m^2 \cdot g^{-1}$ and 150 $m^2 \cdot g^{-1}$.

17. The zeolite adsorbent according to claim 1, wherein the content of non-zeolite phase is between 6% and 11% by weight relative to the total weight of the adsorbent.

18. The zeolite adsorbent according to claim 1, wherein the content of non-zeolite phase is between 6% and 10% by weight relative to the total weight of the adsorbent.

19. The zeolite adsorbent according to claim 1, wherein the FAU zeolite is a zeolite in the form of crystals having:
a number-average diameter between 1.8 μm and 10 μm, and
an outer surface area, measured by nitrogen adsorption, between 40 $m^2 \cdot g^{-1}$ and 200 $m^2 \cdot g^{-1}$.

20. The zeolite adsorbent according to claim 1, which further comprises potassium.

* * * * *